(12) United States Patent
Schmidt

(10) Patent No.: US 9,550,736 B2
(45) Date of Patent: *Jan. 24, 2017

(54) SALT OF BICYCLIC AROMATIC ANIONS FOR LI-ION BATTERIES

(71) Applicant: Arkema France, Colombes (FR)

(72) Inventor: Grégory Schmidt, Mornant (FR)

(73) Assignee: ARKEMA FRANCE, Colombes (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/400,189

(22) PCT Filed: Apr. 26, 2013

(86) PCT No.: PCT/FR2013/050939
§ 371 (c)(1),
(2) Date: Nov. 10, 2014

(87) PCT Pub. No.: WO2013/182768
PCT Pub. Date: Dec. 12, 2013

(65) Prior Publication Data
US 2015/0126746 A1 May 7, 2015

(30) Foreign Application Priority Data

Jun. 4, 2012 (FR) ...................................... 12 55154

(51) Int. Cl.
| | |
|---|---|
| C07D 233/64 | (2006.01) |
| C07D 233/90 | (2006.01) |
| C07D 401/04 | (2006.01) |
| H01M 10/0525 | (2010.01) |
| H01M 10/0568 | (2010.01) |

(52) U.S. Cl.
CPC ........... *C07D 233/90* (2013.01); *C07D 401/04* (2013.01); *H01M 10/0525* (2013.01); *H01M 10/0568* (2013.01); *H01M 2300/0025* (2013.01); *Y02E 60/122* (2013.01); *Y02P 70/54* (2015.11)

(58) Field of Classification Search
CPC ... C07D 233/64; C07D 249/08; C07D 231/12; C07D 233/56; C07D 233/90
USPC ...................................................... 548/336.1
See application file for complete search history.

(56) References Cited

U.S. PATENT DOCUMENTS

| | | | |
|---|---|---|---|
| 5,109,012 A | 4/1992 | Willis et al. | |
| 2004/0009393 A1 | 1/2004 | Kim et al. | |
| 2011/0229769 A1 | 9/2011 | Ihara et al. | |
| 2011/0311884 A1 | 12/2011 | Armand et al. | |
| 2015/0111096 A1* | 4/2015 | Schmidt | ........................ 429/188 |

FOREIGN PATENT DOCUMENTS

| | | |
|---|---|---|
| CN | 102195083 A | 9/2011 |
| CN | 102264926 A | 11/2011 |
| JP | 2011 19508 A | 2/2011 |
| JP | 2012 500833 A | 1/2012 |
| WO | WO 2010/023413 A1 | 3/2010 |

OTHER PUBLICATIONS

Baldwin, J., P. Lumma, F. Novello, G. Ponticello, and J. Sprague "2-Pyridylimidazoles as Inhibitors of Xanthine Oxidase" Journ. Med. Chem. (1977), 20 (9), pp. 1189-1193.*
International Search Report (PCT/ISA/210) mailed on Jul. 12, 2013, by the French Patent Office as the International Searching Authority for International Application No. PCT/FR2013/050939.
U.S. Appl. No. 14/400,165, Schmidt.
Schmidt, U.S. Appl. No. 14/400,165, entitled "Salt of Bicyclic Aromatic Anions for Li-Ion Batteries," filed in the U.S. Patent and Trademark Office on Nov. 10, 2014.
Official Action issued in Chinese Patent Application No. 201380028850.6, Oct. 10, 2015, The State Intellectual Property Office of People's Republic of China, 7 pages (English-language translation).
Niedzicki L. et al. "New type of imidazole based salts designed specifically for Li ion batteries", Electrochimica Acta, vol. 55, No. 4, 2010, pp. 1450-1454.
Scheers J. et al. "Benzimidazole and imidazole lithium salts for battery electrolytes", Journal of Power Sources, vol. 195, No. 18, 2010, pp. 6081-6087.
Office Action (Notice of Reasons for Rejection) issued on Sep. 13, 2016, by the Japanese Patent Office in Japanese Patent Application No. 2015-514550 (4 pages).

* cited by examiner

*Primary Examiner* — Alicia L Otton
*Assistant Examiner* — Sagar Patel
(74) *Attorney, Agent, or Firm* — Buchanan Ingersoll & Rooney P.C.

(57) ABSTRACT

A method for obtaining salts of bicyclic imidazole compounds (V) having general structural formulae in which A represents a monovalent cation, X represents independently a carbon atom, an oxygen atom, a sulphur atom or a nitrogen atom. Also, the associated production method and to the use thereof, in particular as an electrolyte component for batteries.

17 Claims, 2 Drawing Sheets

SALT OF BICYCLIC AROMATIC ANIONS FOR LI-ION BATTERIES

FIELD OF THE INVENTION

The present invention relates to bicyclic imidazole compounds and their salts, to their processes of manufacture and to their uses, in particular as electrolyte component for batteries.

TECHNICAL BACKGROUND

A lithium-ion or sodium-ion battery comprises at least one negative electrode, one positive electrode, one separator and one electrolyte. The electrolyte is composed of a lithium or sodium salt dissolved in a solvent, which is generally a mixture of organic carbonates, in order to have a good compromise between the viscosity and the dielectric constant.

The most widely used salts include lithium hexafluorophosphate ($LiPF_6$), which has many of the numerous qualities required but exhibits the disadvantage of decomposing in the form of hydrogen fluoride gas. This presents safety problems, in particular in the context of the impending use of lithium-ion batteries in specific vehicles.

The prerequisite for having an electrolyte salt is good chemical dissociation between the cation and the anion, which implies a negative charge on the anion which is delocalized or reduced by withdrawing effects.

Salts based on the withdrawing effect have thus been developed, such as LiTFSI (lithium bis(trifluoromethanesulfonyl)imide) and LiFSI (lithium bis(fluorosulfonyl)imide).

Other salts, this time based on the delocalization of the charge, have also been developed, such as LiTDI (lithium 4,5-dicyano-2-(trifluoromethyl)imidazolide), as is taught in the document WO 2010/023413. However, the latter exhibit ionic conductivities which are lower than those mentioned above.

The applicant company has discovered that the presence of a second aromatic ring makes it possible to increase the delocalization of the negative charge and to thus increase this ionic conductivity.

SUMMARY OF THE INVENTION

In that which follows:
DAMN denotes diaminomaleonitrile and is represented by the formula (I):

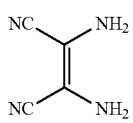

I

The compounds (II) are represented by the expanded general formulae below. They are denoted under (IIa) when the aromatic ring comprises six atoms and under (IIb) for an aromatic ring having five atoms:

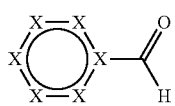

IIa

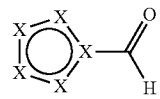

IIb

The compounds (III) are represented by the expanded general formulae below. They are denoted under (IIIa) when the aromatic cycle comprises six atoms and under (IIIb) for an aromatic ring comprising five atoms:

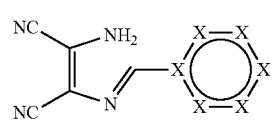

IIIa

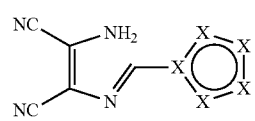

IIIb

The bicyclic imidazole compounds (IV) are represented by the expanded general formulae below. They are denoted under (IVa) when the aromatic ring comprises six atoms and under (IVb) for an aromatic ring comprising five atoms:

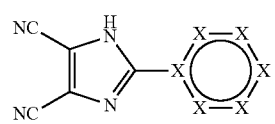

IVa

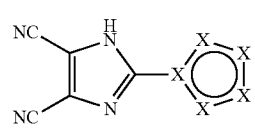

IVb

The salts of the bicyclic imidazole compounds (V) are represented by the expanded general formulae below. They are denoted under (Va) when the aromatic ring comprises six atoms and under (Vb) for an aromatic ring comprising five atoms:

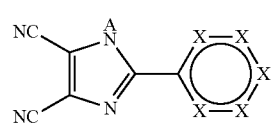

Va

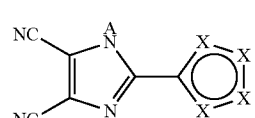

Vb

In the general formulae above, A represents a monovalent cation and X independently represents a carbon atom, an oxygen atom, a sulfur atom, a phosphorus atom or a nitrogen atom.

When X represents a carbon, phosphorus or nitrogen atom, the substituents can independently be electron-withdrawing or electron-donating groups defined by a Hammett parameter (the Hammett parameter is a tabulated constant which is determined for a series of substituent groups by measuring the dissociation constant of the corresponding benzoic acids) of between −0.7 and 1.0. Preferably, the substituents are chosen from a cyano (CN) group, an $R_1$ group, an ether group of $OR_1$ type, an amino group of $N(R_1)_2$ type, an ester group of $CO_2R_1$ type, a sulfonyl group of $SO_2R_1$ type or a phosphonyl group of $PO_2R_1$ type, where $R_1$ has the formula $C_nH_mX'_p$ with n between 0 and 6, m between 0 and 13, X' a halogen (F, Cl, Br and I) and p between 1 and 13.

The invention relates first to the bicyclic imidazole compounds (IV) and their salts (V).

The invention relates secondly to the processes for the manufacture of bicyclic imidazole compounds (IV) and their salts (V).

The invention relates thirdly to the use of the compounds of formula (V).

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein.

DETAILED DESCRIPTION OF THE INVENTION

Figure 1:
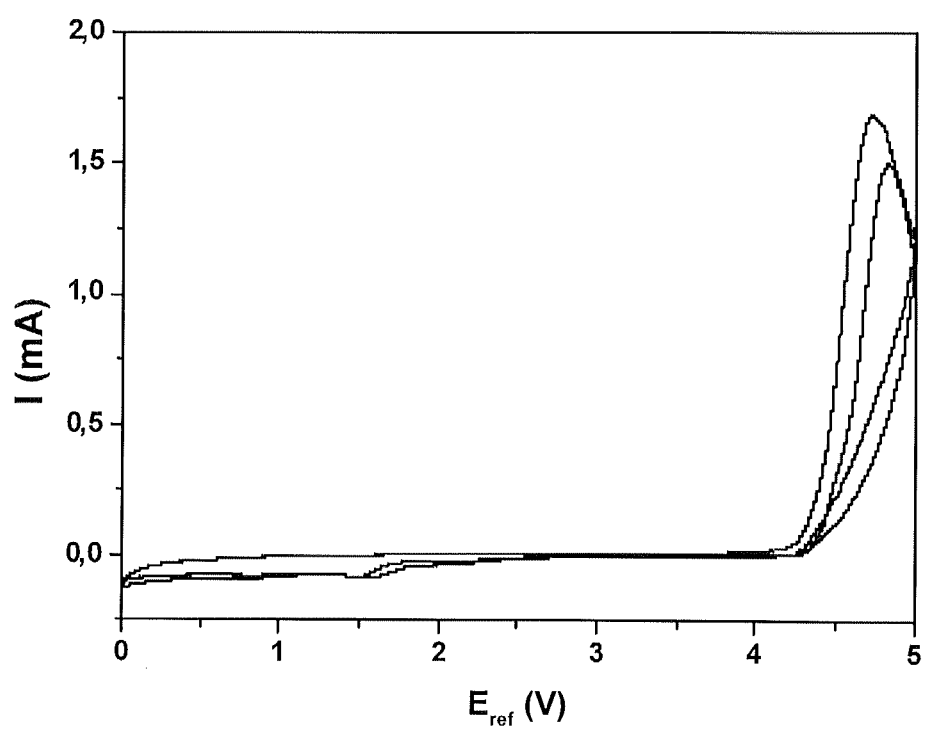
FIG. 1 shows the ionic conductivity of the different concentrations is subsequently measured by impedance spectroscopy.

The invention is now described in more detail and without implied limitation in the description which follows.

The salts of the bicyclic imidazole compounds (V) according to the present invention are represented by the general formula above in which A represents a monovalent cation A, for example an alkali metal.

The preferred alkali metal is chosen from lithium and sodium.

When X in the general formula represents a carbon, phosphorus or nitrogen atom, the salts (V) can be substituted. The preferred substituents are electron-withdrawing or electron-donating groups, in particular those having a Hammett parameter of between −0.7 and 1.

The electron-withdrawing and electron-donating groups which are particularly preferred are chosen from a cyano (CN) group, an $R_1$ group, an ether group of $OR_1$ type, an amino group of $N(R_1)_2$ type, an ester group of $CO_2R_1$ type, a sulfonyl group of $SO_2R_1$ type or a phosphonyl group of $PO_2R_1$ type, where $R_1$ has the formula $C_nH_mX'_p$ with n between 0 and 6, m between 0 and 13, X' a halogen (F, Cl, Br and I) and p between 1 and 13.

Preparation of the Salts of the Bicyclic Imidazole Compounds (Bicyclic Imidazolides) and of the Bicyclic Imidazole Compounds The bicyclic imidazolides (V) can be prepared from the imidazole compounds (IV) by reacting the latter with a base AZ, with A having the same meaning as above and Z representing a hydride, hydroxide or carbonate anion. Preferably, AZ is chosen from lithium hydride, lithium carbonate, lithium hydroxide, sodium hydride, sodium carbonate, sodium hydroxide and the combinations of these.

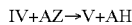

IV+AZ→V+AH

The compounds (IV) can be prepared from the condensation of an aromatic aldehyde of general formula (II) and DAMN (I).

The process for the preparation of the bicyclic imidazole compounds (IV) comprises (i) a stage of reaction of DAMN of formula (I) with an aromatic aldehyde of general formula (II) at a temperature of between 0 and 80° C., preferably from 10 to 50° C., more preferably from 20 to 30° C., optionally in the presence of a solvent, to give a compound of formula (III), followed (ii) by a stage of dehydrogenation of the compound of formula (III).

DAMN+II→III+H$_2$O       (i)

III−H$_2$→IV       (ii)

Stage (i) is preferably carried out in the presence of a solvent. Any compound which makes it possible to dissolve the reactant(s) can be used as solvent. Mention may be made, by way of indication, of dioxane, acetonitrile or ethanol.

When stage (i) is carried out in the presence of a solvent, the concentration of DAMN in the reaction medium is preferably from 0.001 to 2 mol/l, more preferably from 0.1 mol/l to 1 mol/l. The molar ratio of the compound (I) to the compound (II) is preferably from 0.25 to 1.5, more preferably from 0.5 to 1.25.

The duration of stage (i) is preferably from 1 to 12 hours, more particularly from 1 to 5 hours, for example approximately 2 hours.

Preferably, stage (i) is carried out in the presence of an acid catalyst, optionally by addition of sulfuric acid or of a carboxylic acid, such as trifluoroacetic acid, acetic acid or benzoic acid, to the reaction medium.

According to one embodiment of the invention, the temperature of the reaction can be constant throughout the first stage.

According to another embodiment of the invention, the temperature is increasing throughout stage (i).

Stage (ii) can be carried out in the presence of a compound capable of reacting with hydrogen, such as oxygen, hydrogen peroxide and peroxides, N-chlorosuccinimide, N-bromosuccinimide, hypochlorous acid, hypofluorous acid or compounds having a quinone-type backbone.

On conclusion of this reaction, the bicyclic imidazole compound of formula (IV) is preferably isolated and purified.

Thus, the reaction medium can be evaporated and the imidazole (III) recrystallized from water to be subsequently recovered by filtration. The solid obtained can be dissolved in an aqueous solution of base AZ, preferably a lithium or sodium base, with a concentration ranging from 10$^5$ mol/l to the saturation concentration. Once the compound salt of formula (IV) is formed, the solution can undergo several treatments with active charcoal. The solution can subsequently be evaporated to give the salt of formula (IV).

Preparation of an Electrolyte

The compounds of formula (V) can be used in the preparation of an electrolyte by dissolving them in an appropriate solvent.

The solvent can be composed of at least one compound chosen from carbonates, glymes, nitriles and sulfones.

Mention may in particular be made, as carbonate, of ethylene carbonate, dimethyl carbonate, ethyl methyl carbonate, diethyl carbonate, propylene carbonate or glycerol carbonate.

Mention may in particular be made, as glymes, of ethylene glycol dimethyl ether, diethylene glycol dimethyl ether, dipropylene glycol dimethyl ether, diethylene glycol diethyl ether, triethylene glycol dimethyl ether, diethylene glycol dibutyl ether, tetraethylene glycol dimethyl ether and diethylene glycol t-butyl methyl ether.

Mention may in particular be made, as nitriles, of acetonitrile, propionitrile, butyronitrile, methoxypropionitrile, isobutyronitrile and the fluorinated compounds deriving from the above compounds.

Mention may in particular be made, as sulfones, of dimethyl sulfone, sulfolane, ethyl methyl sulfone, propyl methyl sulfone, isopropyl methyl sulfone, isopropyl ethyl sulfone, tert-butyl ethyl sulfone, tert-butyl methyl sulfone and tert-butyl propyl sulfone.

The solvent is preferably composed of a mixture of compounds, advantageously from 2 to 5, chosen from the abovementioned carbonates and/or glymes and/or sulfones.

The proportions by weight of each of the compounds constituting the solvent are preferably between 1 and 10, with respect to the constituent in smallest amount, more preferably between 1 and 8.

The concentration of compound of formula (V) in the electrolyte is preferably from 0.1 mol/l to 5 mol/l, more preferably from 0.2 mol/l to 2.5 mol/l. Preferably, the electrolyte is composed of a mixture of at least two lithium salts chosen from the imidazolide salt (IV), $LiPF_6$, $LiBF_4$, $CF_3COOLi$, $CF_3SO_2Li$, LiTFSI (lithium bis(trifluoromethanesulfonyl)imide), LiFSI (lithium bis(fluorosulfonyl)imide), LiTDI (lithium 4,5-dicyano-2-(trifluoromethyl)imidazolide) and LiPDI (lithium 4,5-dicyano-2-(pentafluoroethyl) imidazolide). The amount of each lithium salt present in the mixture can vary within wide limits and generally represents between 0.1% and 99.9% by weight, with respect to the total weight of the salts present in the mixture, preferably between 1% and 99% by weight.

EXAMPLE

The following example illustrates the invention without limiting it.

A few drops of sulfuric acid are added to 50 ml of acetonitrile comprising 1.19 g of predissolved DAMN and 1.47 g of p-CN-benzaldehyde. A yellow precipitate then appears. The reaction mixture is left stirring for 3 hours. The solution is filtered off and the solid is rinsed with acetonitrile and then ether. The solid is subsequently dried under vacuum at 110° C.

0.94 g of $K_2CO_3$ and then 0.90 g of N-chlorosuccinimide are added to 1.0 g of the solid obtained above dissolved in 25 ml of dimethylformamide in a 50 ml round-bottomed flask. The solution is stirred at ambient temperature overnight. 150 ml of water are added at the end of the reaction. The solution is acidified to pH=1 with sulfuric acid. The aqueous phase is then extracted with 2 times 100 ml of ethyl acetate. The organic phases are dried and then evaporated. The NMR analysis of the residue shows the presence of the desired product. The residue is taken up in water in the presence of an excess of lithium carbonate. The solution is stirred at ambient temperature for 3 hours. The solution is filtered and then extracted with 2 times 250 ml of ether. The aqueous phase is subsequently treated with active charcoal at 50° C. for 2 hours. The solution is filtered and then evaporated. The residue is subsequently taken up in acetonitrile and the insoluble part, corresponding to lithium carbonate, is removed by filtration. The filtrate is then evaporated and gives a yellow solid which is the lithium salt of following formula:

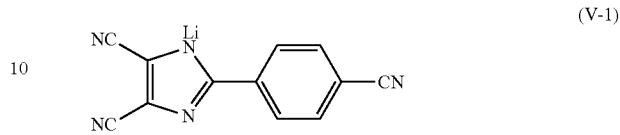

(V-1)

Figure 2:
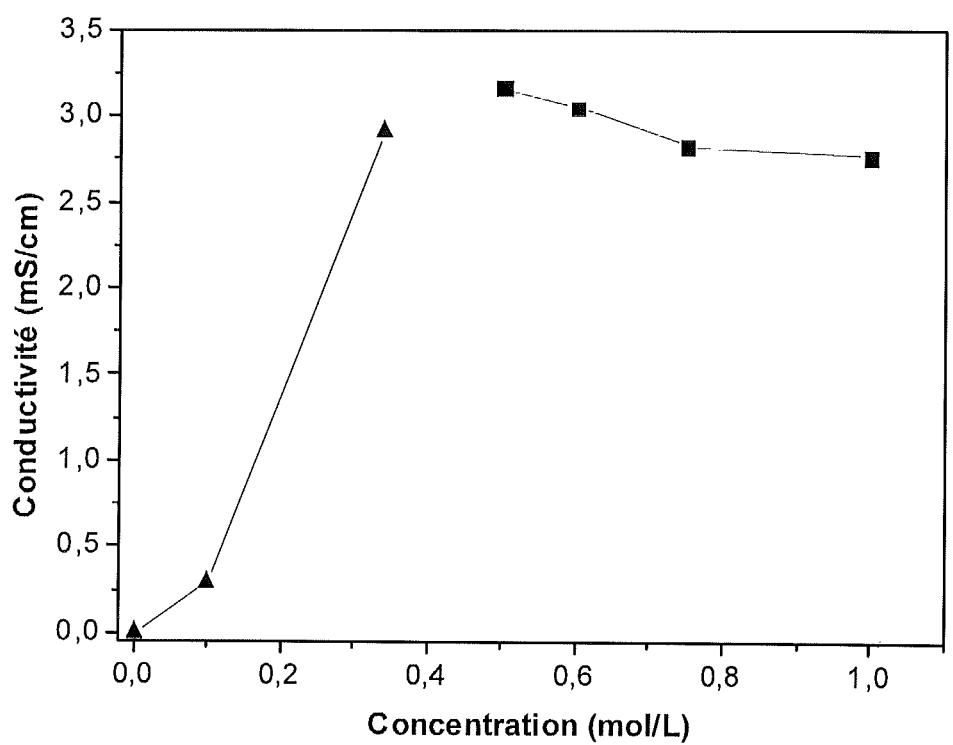
FIG. 2 shows the electrochemical stability of the salt (V1) with respect to Li+/Li is subsequently determined by cyclic voltammetry of a 1 mol/l solution of the salt (V1) in an ethylene carbonate and dimethyl carbonate mixture with a ratio by weight of 1.

The salt (V-1) is subsequently dissolved at different concentrations in a mixture of ethylene carbonate and of dimethyl carbonate with a ratio by weight of 1. The ionic conductivity of the different concentrations is subsequently measured by impedance spectroscopy (FIG. 1). The electrochemical stability of the salt (V-1) with respect to $Li^+/Li$ is subsequently determined by cyclic voltammetry of a 1 mol/l solution of the salt (V-1) in an ethylene carbonate and dimethyl carbonate mixture with a ratio by weight of 1 (FIG. 2).

The invention claimed is:

1. A process for the preparation of a salt of a bicyclic imidazole compound of general formula (Va), wherein general formula (Va) is represented by the general formula below:

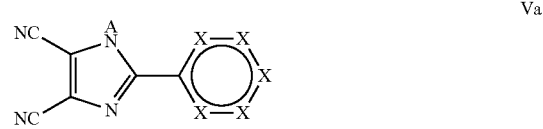

Va wherein A represents a monovalent alkali metal cation and X independently represents a carbon atom, a phosphorus atom or a nitrogen atom, wherein an imidazole compound of formula (IVa):

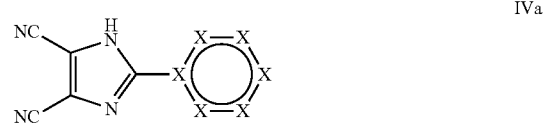

IVa is reacted with a base AZ, wherein A is the same monovalent cation as in general formula (Va) and Z is a hydride, hydroxide or carbonate anion.

2. The process for the preparation of a salt as claimed in claim 1, wherein a substituent of the carbon or the nitrogen is an electron-withdrawing or electron-donating group having a Hammett parameter of 0.7 to 1.

3. The process for the preparation of a salt as claimed in claim 2, wherein the electron-withdrawing or electron-donating group is chosen from hydrogen, fluorine, a cyano (CN) group, a trifluoromethyl ($CF_3$) group, a trifluoromethoxy ($OCF_3$) group or a methoxy ($OCH_3$) group.

4. The process as claimed in claim 1, wherein the base AZ is selected from the group consisting of lithium hydride, lithium carbonate, lithium hydroxide, sodium hydride, sodium carbonate, and sodium hydroxide, or combinations thereof.

5. The process as claimed in claim 1, wherein the imidazole compound of formula (IVa) is obtained by condensation of an aromatic aldehyde of formula (IIa):

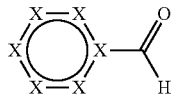

with diaminomaleonitrile, followed by dehydrogenation of the intermediate compound thus obtained of formula (IIIa):

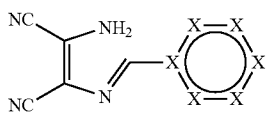

6. The process as claimed in claim 5, comprising (i) a stage of reaction of diaminomaleonitrile with the aromatic aldehyde of formula (IIa) at a temperature of 0 to 80° C., optionally in the presence of a solvent, to give a compound of formula (IIIa), followed (ii) by a stage of dehydrogenation of said compound of formula (IIIa).

7. The process as claimed in claim 6, wherein stage (i) is carried out in the presence of a solvent.

8. The process as claimed in claim 7, wherein the solvent is chosen from dioxane, acetonitrile or ethanol.

9. The process as claimed in claim 6, wherein stage (i) is carried out in the presence of an acid catalyst.

10. The process as claimed in claim 9, wherein the acid catalyst is chosen from sulfuric acid, trifluoroacetic acid, acetic acid or benzoic acid.

11. The process as claimed in claim 6, wherein stage (ii) of dehydrogenation is carried out in the presence of an oxidizing agent.

12. The process for the preparation of a salt as claimed in claim 1, wherein the monovalent cation A is lithium or sodium.

13. The process for the preparation of a salt as claimed in claim 1, wherein the carbon or the nitrogen is substituted by electron-withdrawing or electron-donating groups having a Hammett parameter of 0.7 to 1 and chosen from a cyano (CN) group, an $R_1$ group, an ether group of $OR_1$ type, an amino group of $N(R_1)_2$ type, an ester group of $CO_2R_1$ type, a sulfonyl group of $SO_2R_1$ type or a phosphonyl group of $PO_2R_1$ type, where $R_1$ has the formula $C_nH_mX'_p$ wherein n is 0 to 6, m is 0 to 13, X' is a halogen selected from the group consisting of F, Cl, Br, and I, and p is 1 to 13.

14. The process as claimed in claim 5, comprising (i) a stage of reaction of diaminomaleonitrile with the aromatic aldehyde of formula (IIa) at a temperature of 10 to 50° C., optionally in the presence of a solvent, to give a compound of formula (IIIa), followed (ii) by a stage of dehydrogenation of said compound of formula (IIIa).

15. The process as claimed in claim 5, comprising (i) a stage of reaction of diaminomaleonitrile with the aromatic aldehyde of formula (IIa) at a temperature of 20 to 30° C., optionally in the presence of a solvent, to give a compound of formula (IIIa), followed (ii) by a stage of dehydrogenation of said compound of formula (IIIa).

16. The process as claimed in claim 6, wherein stage (ii) of dehydrogenation is carried out in the presence of an oxidizing agent selected from oxygen, hydrogen peroxide, peroxides, N-chlorosuccinimide, N-bromosuccinimide, hypochlorous acid, hypofluorous acid or compounds comprising a quinone-type backbone.

17. A process for the preparation of a salt of a bicyclic imidazole compound of general formula (Va),
wherein general formula (Va) is represented by the general formula below:

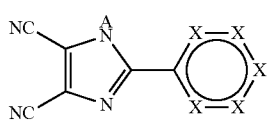

wherein A represents a monovalent alkali metal cation and X independently represents a carbon atom, a phosphorus atom or a nitrogen atom,
wherein an imidazole compound of formula (IVa):

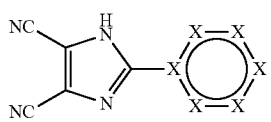

is reacted with a base AZ, wherein A is the same monovalent cation as in general formula (Va) and Z is a hydride, hydroxide or carbonate anion, and
wherein the imidazole compound of formula (IVa) is obtained by condensation of an aromatic aldehyde of a general formula (IIa):

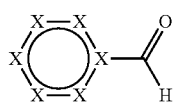

with diaminomaleonitrile, followed by dehydrogenation of the intermediate compound thus obtained of a general formula (IIIa):

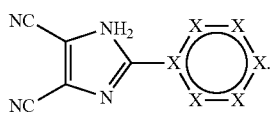

* * * * *